US00PP27843P2

(12) United States Plant Patent
Beekenkamp

(10) Patent No.: US PP27,843 P2
(45) Date of Patent: Apr. 4, 2017

(54) ***CELOSIA* PLANT NAMED 'BKCELFLM'**

(50) Latin Name: *Celosia plumosa*
Varietal Denomination: BKCELFLM

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 14/757,004

(22) Filed: Nov. 6, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — C. A. Whealy

(57) ABSTRACT

A new and distinct cultivar of *Celosia* plant named 'BKCELFLM', characterized by its broadly upright plant habit; freely basal branching habit; medium green-colored leaves; freely flowering habit; bright lime green-colored flowers arranged on conical compound spikes; and good interiorscape and garden performance.

2 Drawing Sheets

Botanical designation: *Celosia plumosa.*
Cultivar denomination: 'BKCELFLM'.

BACKGROUND OF THE INVENTION

The present invention relates to a new and distinct *Celosia* plant, botanically known as *Celosia plumosa* and hereinafter referred to by the name 'BKCELFLM'.

The new *Celosia* plant is a product of a planned breeding program conducted by the Inventor in Maasdijk, The Netherlands. The objective of the breeding program is to create new *Celosia* plants that have unique and attractive flowers, long flowering period and good interiorscape and garden performance.

The new *Celosia* plant originated from an open-pollination in June, 2011 in Maasdijk, The Netherlands of a proprietary selection of *Celosia plumosa* identified as code number 1401022, not patented, as the female, or seed, parent with an unknown selection of *Celosia plumosa* as the male, or pollen, parent. The new *Celosia* plant was discovered and selected by the Inventor as a single flowering plant from within the progeny of the stated open-pollination in a controlled environment in Maasdijk, The Netherlands in April, 2012.

Asexual reproduction of the new *Celosia* plant by cuttings in a controlled environment in Maasdijk, The Netherlands since May, 2012 has shown that the unique features of this new *Celosia* plant are stable and reproduced true to type in successive generations.

SUMMARY OF THE INVENTION

Plants of the new *Celosia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BKCELFLM'. These characteristics in combination distinguish 'BKCELFLM' as a new and distinct *Celosia* plant:

1. Broadly upright plant habit.
2. Freely basal branching habit.
3. Medium green-colored leaves.
4. Freely flowering habit.
5. Bright lime green-colored flowers arranged on conical compound spikes.
6. Good interiorscape and garden performance.

Plants of the new *Celosia* differ from plants of the female parent selection in the following characteristics:

1. Plants of the new *Celosia* are taller than plants of the female parent selection.
2. Leaves of plants of the new *Celosia* are broader than leaves of plants of the female parent selection.
3. Plants of the new *Celosia* and the female parent selection differ in leaf color as plants of the female parent selection have green and red-colored leaves.
4. Plants of the new *Celosia* and the female parent selection differ in flower color as plants of the female parent selection have purple-colored flowers.

Plants of the new *Celosia* can be compared to plants of *Celosia plumosa* 'Flame', not patented. In side-by-side comparisons, plants of the new *Celosia* differ primarily from 'Flame' in the following characteristics:

1. Leaves of plants of the new *Celosia* are lighter green in color than leaves of plants of 'Flame'.
2. Plants of the new *Celosia* flower earlier than plants of 'Flame'.
3. Plants of the new *Celosia* and 'Flame' differ in flower color as plants of 'Flame' have dark orange-colored flowers.

BRIEF DESCRIPTION OF THE PHOTOGRAPHS

The accompanying colored photographs illustrate the overall appearance of the new *Celosia* plant showing the colors as true as it is reasonably possible to obtain in colored reproductions of this type. Colors in the photographs may differ slightly from the color values cited in the detailed botanical description which accurately describe the colors of the new *Celosia* plant.

The photograph on the first sheet comprises a side perspective view of a typical flowering plant of 'BKCELFLM' grown in a container.

The photograph on the second sheet is a close-up view of a typical inflorescence of 'BKCELFLM'.

DETAILED BOTANICAL DESCRIPTION

The aforementioned photographs and following observations, measurements and values describe plants grown in 12-cm containers during the winter in a glass-covered greenhouse in Maasdijk, The Netherlands and under commercial cultural practices typical of *Celosia* production. During the production of the plants, day temperatures ranged from about 17° C. to 18° C. and night temperatures ranged from about 16° C. to 17° C. Plants were pinched one time and were 13 weeks old when the photographs and description were taken. In the following description, color references are made to The Royal Horticultural Society Colour Chart, 2007 Edition, except where general terms of ordinary dictionary significance are used.

Botanical classification: *Celosia plumosa* 'BKCELFLM'.

Parentage:

*Female, or seed, parent*.—Proprietary selection of *Celosia plumosa* identified as code number 1401022, not patented.

*Male, or pollen, parent*.—Unknown selection of *Celosia plumosa*, not patented.

Propagation:

*Type*.—By cuttings.

*Time to initiate roots, summer*.—About 16 days at temperatures ranging from about 19° C. to 21° C.

*Time to initiate roots, winter*.—About 19 days at temperatures ranging from about 19° C. to 21° C.

*Time to produce a rooted young plant, summer*.—About 21 days at temperatures ranging from about 19° C. to 21° C.

*Time to produce a rooted young plant, winter*.—About 23 days at temperatures ranging from about 19° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Herbaceous annual typically grown as a potted plant; broadly upright plant habit; inverted triangle; freely branching habit with about four basal branches each with several lateral branches developing per plant; moderately vigorous growth habit.

*Plant height*.—About 29.2 cm.

*Plant width* (*spread*).—About 33.3 cm.

*Lateral branches*.—Length: About 7.8 cm. Diameter: About 8 mm. Internode length: About 3 mm to 20 mm. Strength: Moderately strong. Texture: Smooth, glabrous. Luster: Moderately glossy. Color, developing: Close to 145B. Color, fully developed: Close to 151A to 151B.

Leaf description:

*Arrangement*.—Alternate; simple.

*Length*.—About 11.2 cm.

*Width*.—About 5.3 cm.

*Shape*.—Ovate.

*Apex*.—Apiculate.

*Base*.—Attenuate.

*Margin*.—Entire; undulate.

*Texture, upper surface*.—Leaf blade, smooth, glabrous; main vein, densely pubescent.

*Texture, lower surface*.—Smooth, glabrous.

*Luster, upper surface*.—Slightly glossy.

*Luster, lower surface*.—Moderately glossy.

*Venation pattern*.—Pinnate.

*Color*.—Developing leaves, upper and lower surfaces: Close to 145A. Fully expanded leaves, upper surface: Close to 137A to 137B; towards the apex, tinged with close to N137A; venation, close to 147D. Fully expanded leaves, lower surface: Close to between 138B and 147B; venation, close to 145B.

*Petioles*.—Length: About 2.5 cm. Diameter: About 2.5 mm. Texture, upper and lower surfaces: Smooth, glabrous. Color, upper and lower surfaces: Close to 145A.

Flower description:

*Flower type and arrangement*.—Single rotate flowers arranged in conical terminal compound spikes; flowers sessile; flowers face upright to slightly outwardly; flowers do not fully open and remain in flower bud form.

*Flowering habit*.—Freely flowering habit with about 5,000 flowers developing per inflorescence.

*Fragrance*.—None detected.

*Natural flowering season*.—Plants begin flowering about 90 days after planting; flowering continuous from spring into the autumn in The Netherlands.

*Postproduction longevity*.—Inflorescences of the new Celosia have good longevity and plants maintain good substance for about 70 days; flowers not persistent.

*Inflorescence height*.—About 7.3 cm.

*Inflorescence diameter*.—About 4.2 cm.

*Flower diameter*.—About 0.5 mm.

*Flower height*.—About 2.5 mm.

*Flower buds*.—Length: About 2.5 mm. Diameter: About 0.5 mm. Shape: Narrowly ovoid. Texture: Smooth, glabrous. Color: Close to 145C.

*Petals*.—None observed.

*Sepals*.—Quantity per flower: Typically eight. Length: About 2 mm. Width: About 0.3 mm. Shape: Narrowly ovate. Apex: Narrowly acute. Margin: Entire. Texture, inner and outer surfaces: Smooth, glabrous. Luster, inner and outer surfaces: Glossy. Color: When opening, inner and outer surfaces: Close to 145C. Fully opened, inner and outer surfaces: Close to 145C to 145D; color does not fade with development.

*Flower bracts*.—Quantity per flower: Typically one. Length: About 4 mm. Width: About 0.3 mm. Shape: Lanceolate. Apex: Narrowly acute. Margin: Entire.

Texture, upper and lower surfaces: Smooth, glabrous. Color, upper and lower surfaces: Close to 145C.

*Peduncles*.—Length: About 5.8 mm. Diameter: About 3 mm. Angle: Upright to about 45° from vertical. Strength: Moderately strong. Texture: Smooth, glabrous. Luster: Moderately glossy. Color: Close to 145B.

*Reproductive organs*.—Stamens: Stamen development has not been observed on plants of the new *Celosia*. Pistils: Quantity per flower: One. Length: About 1 mm. Stigma shape: Club-shaped. Stigma color: Close to 145C to 145D. Style length: About 0.8 mm. Style color: Close to 145C to 145D. Ovary color: Close to 145C to 145D.

*Seeds and fruits*.—Seed and fruit development have not been observed on plants of the new *Celosia*.

Disease & pest resistance: Plants of the new *Celosia* have not been observed to be resistant to pathogens and pests common to *Celosia* plants.

Garden performance: Plants of the new *Celosia* have been observed to have good garden performance and tolerate rain, wind and high temperatures of about 35° C. and to be hardy to USDA Hardiness Zone 9.

It is claimed:

1. A new and distinct *Celosia* plant named 'BKCELFLM' as illustrated and described.

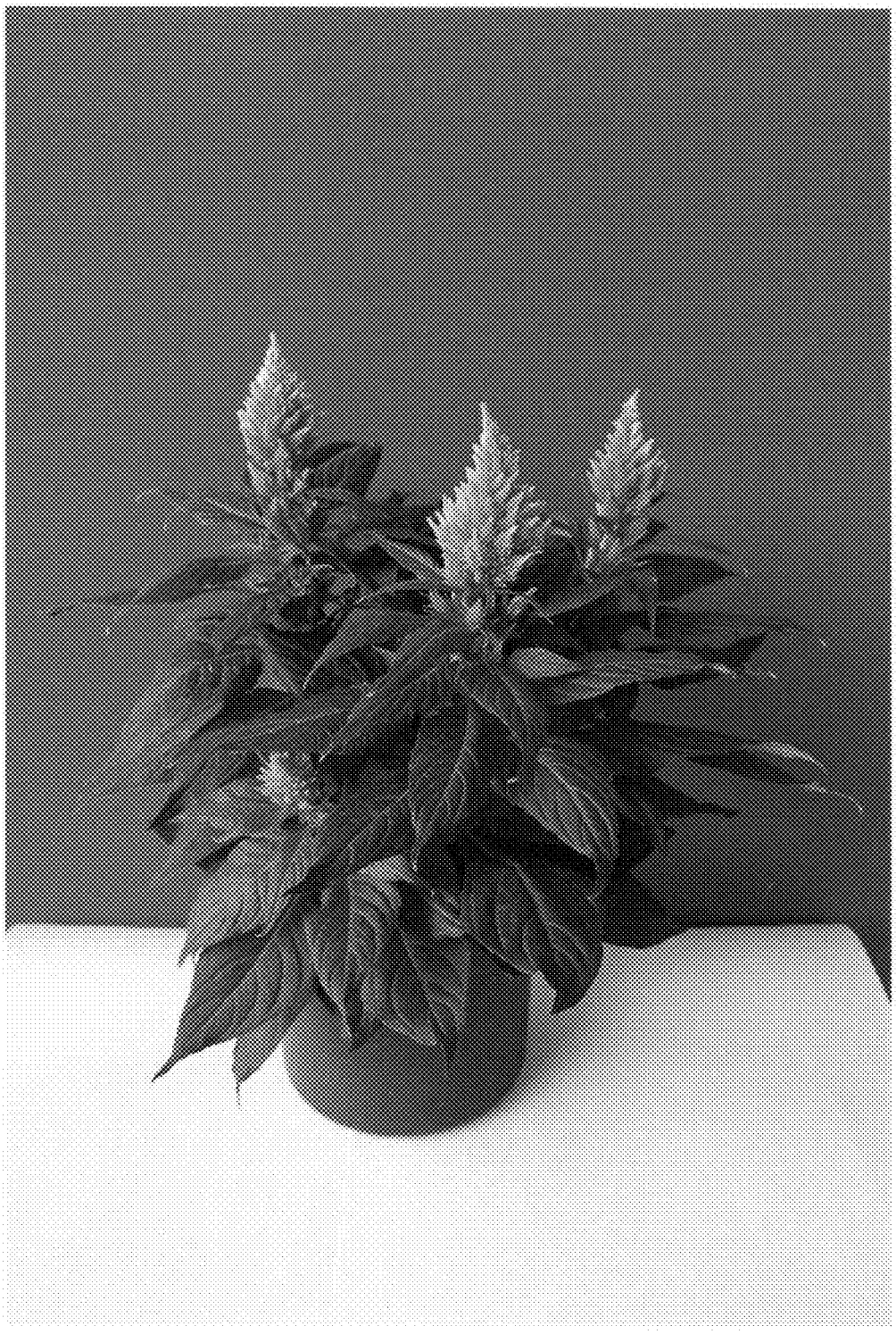

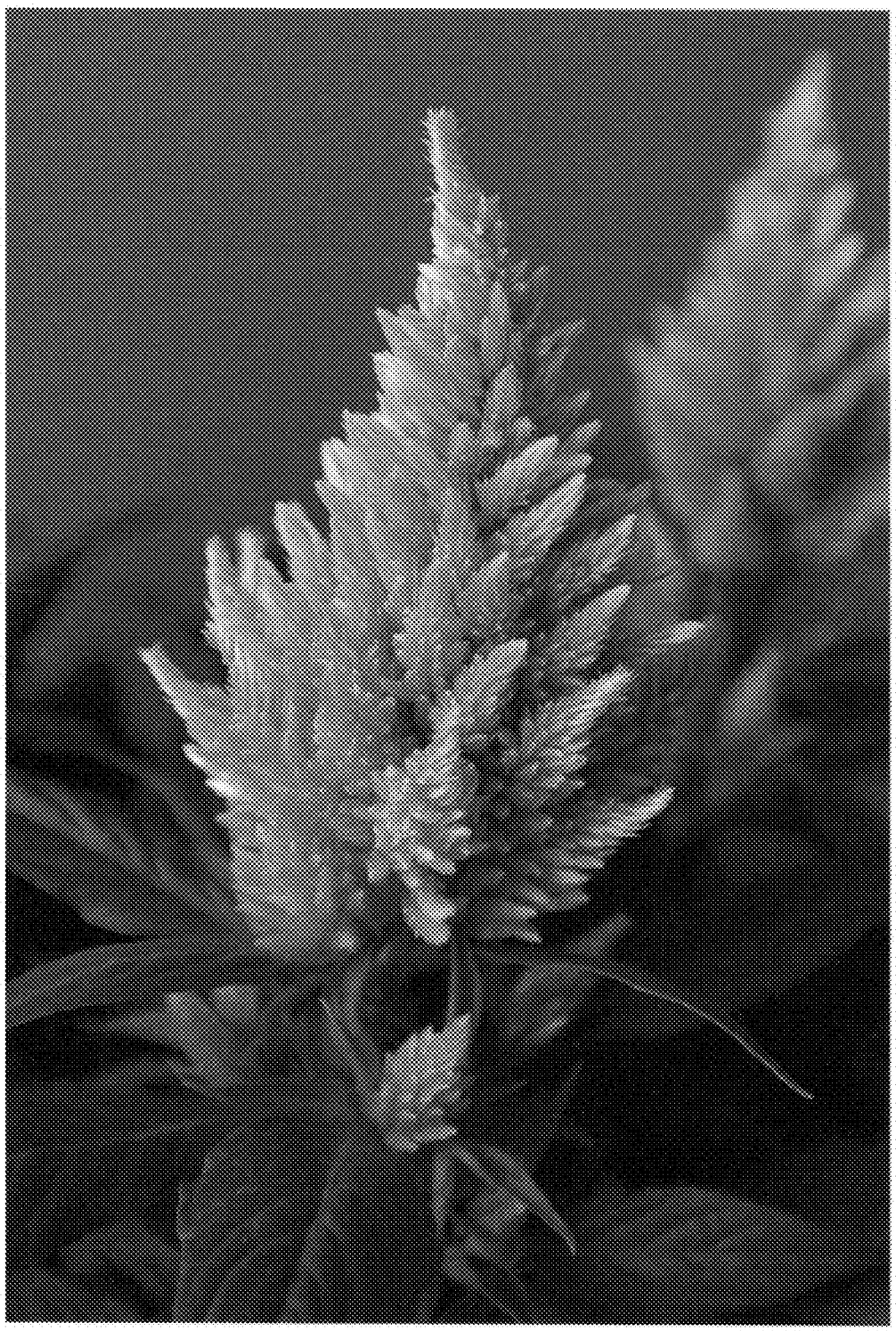

* * * * *